United States Patent [19]

Hopkins et al.

[11] Patent Number: 5,449,486
[45] Date of Patent: Sep. 12, 1995

[54] METHOD OF FORMING A FACIAL PROPHYLACTIC

[76] Inventors: Laron Hopkins, 72 Gamble Avenue, Apt. 611, East York, Ontario, Canada, M4K 2H2; Jennifer A. Neves, 428 King St.; Peter R. Horn, 428 King St. Unit 1, both of E. Cobourg Ontario, Canada, K9A 1M6

[21] Appl. No.: 171,475

[22] Filed: Oct. 7, 1992

Related U.S. Application Data

[63] Continuation-in-part of Ser. No. 727,377, Jul. 5, 1991, abandoned, which is a continuation of Ser. No. 402,370, Sep. 5, 1989, abandoned.

[51] Int. Cl.⁶ .................... A61F 13/12; B29C 39/12; B29C 39/42
[52] U.S. Cl. .................... 264/500; 264/299; 128/859; 128/918
[58] Field of Search ............... 264/500, DIG. 52, 293, 264/296, 303, 319, 299, 300; 128/842, 844, 858, 859, 918

[56] References Cited

U.S. PATENT DOCUMENTS

| | | | |
|---|---|---|---|
| 1,861,673 | 6/1932 | Wilhelmi | 264/DIG. 52 |
| 1,884,342 | 10/1932 | Stelzner | 264/DIG. 52 |
| 2,300,912 | 11/1942 | Dodge et al. | 264/DIG. 52 |
| 2,370,294 | 2/1945 | Dodge | 264/DIG. 52 |
| 2,415,391 | 2/1947 | Lovell et al. | 264/DIG. 52 |
| 2,667,869 | 2/1954 | D'Elia | 128/206.13 |
| 4,815,456 | 3/1989 | Rubin et al. | 128/859 |
| 4,949,731 | 8/1990 | Harding | 128/842 |
| 4,974,605 | 12/1990 | Esqueda | 128/857 |
| 5,016,649 | 5/1991 | Johnson | 128/859 |
| 5,306,460 | 4/1994 | Hidawa et al. | 264/500 |
| 5,318,043 | 6/1994 | Burr et al. | 128/859 |

FOREIGN PATENT DOCUMENTS 192960 11/1964 Sweden .................. 264/500

*Primary Examiner*—Catherine Timm

[57] ABSTRACT

A method of manufacturing a facial prophylactic from a fluid impervious stretchable material comprises working the material while in a liquid state to regions of different thicknesses and elasticities to form a mask having a thinner tongue receiving portion generally centrally of the mask and a thicker main portion peripherally of the tongue receiving portion. The overall mask has a one piece construction and is free of any seams penetrating through the mask.

11 Claims, 4 Drawing Sheets

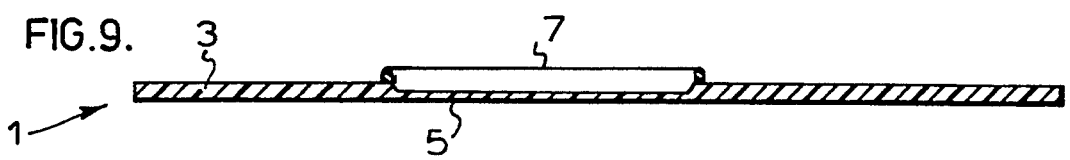
FIG. 9.
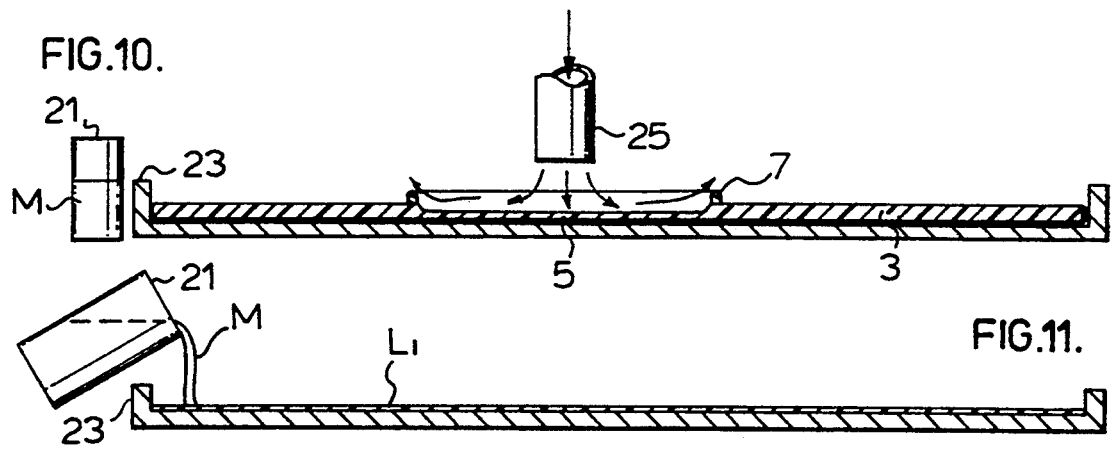
FIG. 10.
FIG. 11.
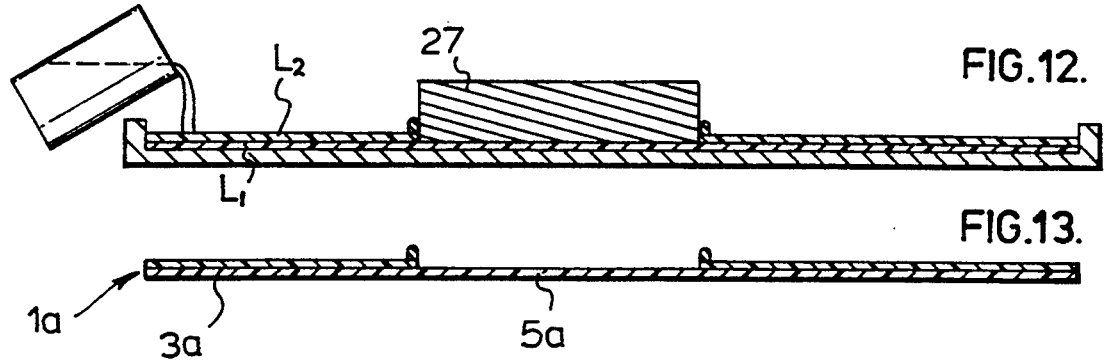
FIG. 12.
FIG. 13.

METHOD OF FORMING A FACIAL PROPHYLACTIC

This is a continuation in part of U.S. patent application Ser. No. 07/727,377, filed Jul. 5, 1991 now abandoned which was a continuation of U.S. patent application Ser. No. 07/402,370, filed Sep. 5, 1989 now abandoned in the name of Laron Hopkins, Jennifer A. Neves and Peter R. Horn.

FIELD OF THE INVENTION

The present invention relates to a prophylactic specifically designed to cover ones face while allowing safe oral sex and a method of manufacturing a facial prophylactic.

BACKGROUND OF THE INVENTION

Until very recently, even the mention of oral sex has been frowned upon. However, this is not the reality of the situation and many cases of mouth diseases are arising as the result of oral sex. The number of such cases has risen dramatically due to the recent AIDS scare where people often feel that AIDS can be avoided through oral sex. According to a recent doctor survey, patients are now being seen on a daily basis with diseases such as syphilis, gonorrhea, herpes and even orally contracted AIDS. There is therefore a very strong need for the development of a facial prophylactic.

SUMMARY OF THE INVENTION

A method of manufacturing a facial prophylactic from a fluid impervious stretchable material comprises working without penetrating the material while in a liquid state to regions of different thicknesses and elasticities to form a mask having a thinner tongue receiving portion generally centrally of the mask and a thicker main mask portion peripherally of the tongue receiving portion. The method results in a one piece facial prophylactic mask without any seams through the mask at the interface between the tongue receiving portion and the main portion of the mask.

A mask made in accordance with the present invention allows oral sex but does not permit skin to skin contact thereby avoiding the possibility of communicating diseases which might otherwise result because of such skin to skin contact.

BRIEF DESCRIPTION OF THE DRAWINGS

The above as well as other advantages and features of the present invention will be described in greater detail according to the preferred embodiments of the invention are shown in the drawings, in which:

FIG. 9 is a sectional view along the lines 9—9 of FIG. 1;

FIG. 10 is a sectional view of the mask the same as that shown in FIG. 9 and further showing a method of manufacturing the mask;

FIG. 11 is a sectional view through a mold showing the first stage of an alternate method of manufacturing a mask according to a further preferred embodiment of the present invention;

FIG. 12 is a further sectional view through the mold shown in FIG. 11 during the second stage of manufacturing of the mask.

FIG. 13 is a sectional view through a mask made in accordance with the method shown in FIGS. 11 and 12 of the drawings.

DETAILED DESCRIPTION OF THE PREFERRED EMBODIMENTS

Figure 1:
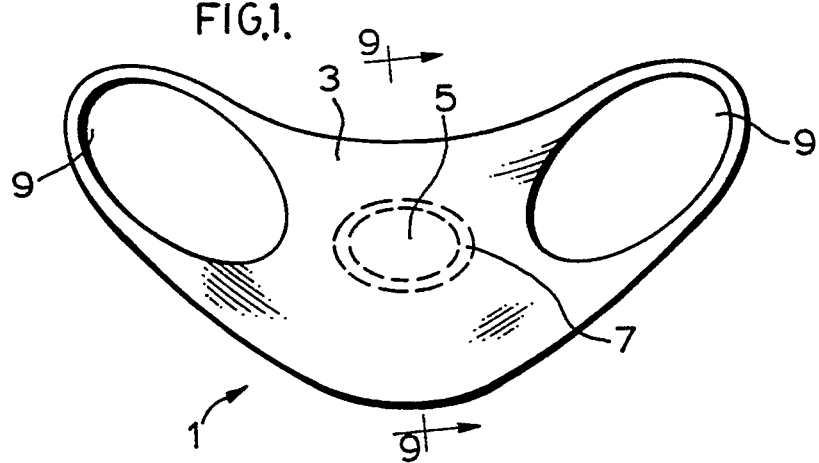
FIG. 1 is a plan view of a facial prophylactic according to a preferred embodiment of the present invention.
Figure 2:
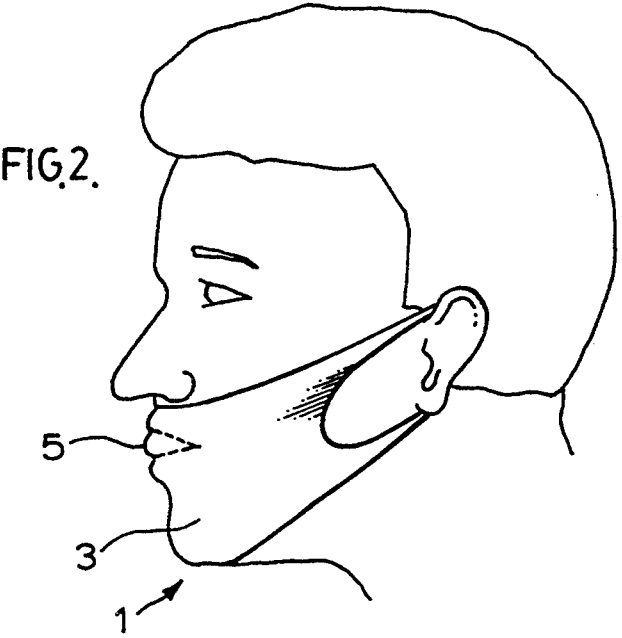
FIGS. 2 and 3 are side views of a person using the facial prophylactic of FIG. 1.
Figure 3:
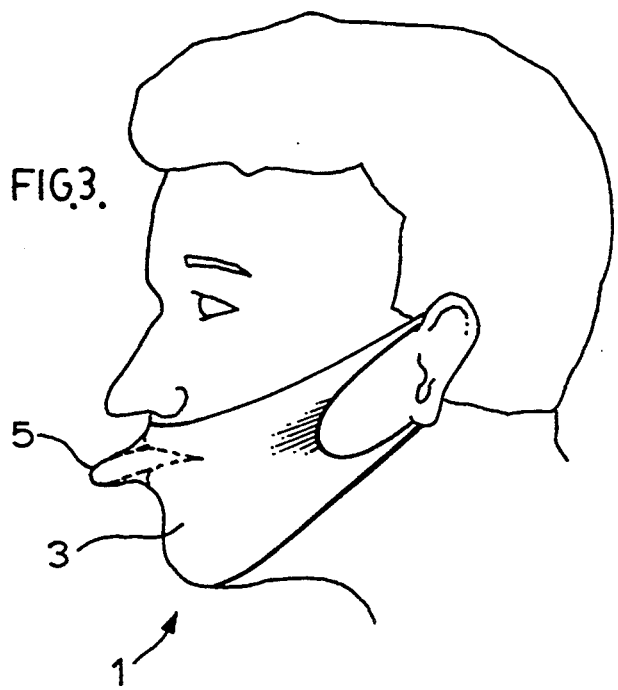
Figure 4A:
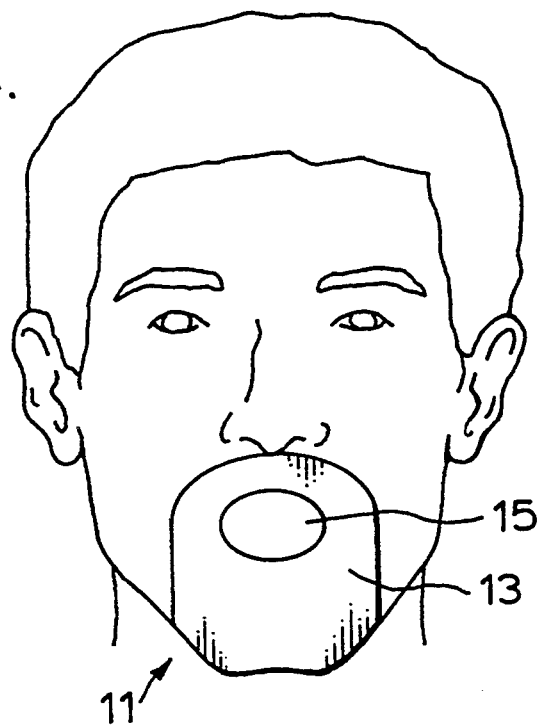
FIG. 4 is a front view of a person using a facial prophylactic according to a different preferred embodiment of the present invention.
Figure 4B:
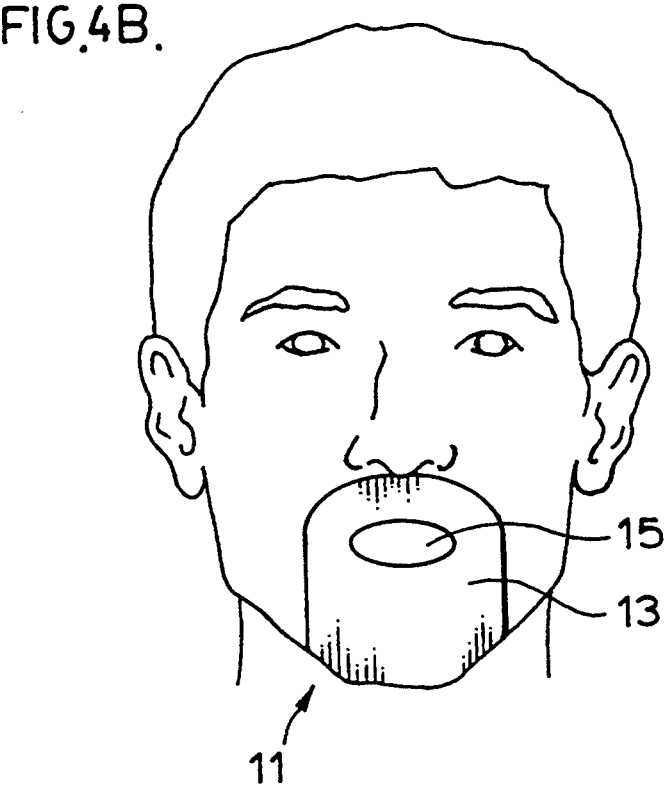
Figure 5:
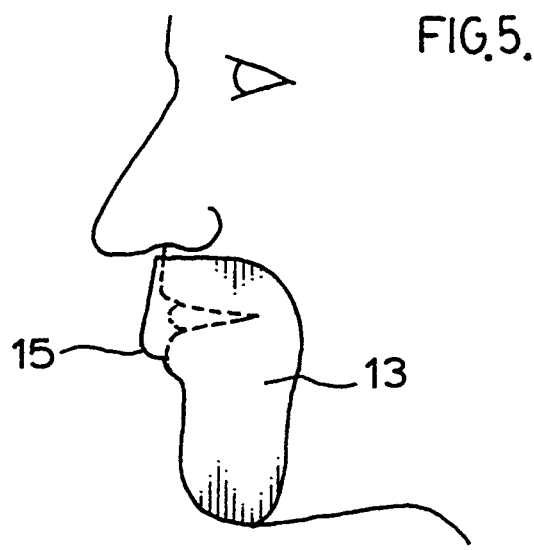
FIGS. 5 and 6 are side views of the facial prophylactic of FIG. 4 in different positions of use.
Figure 6:
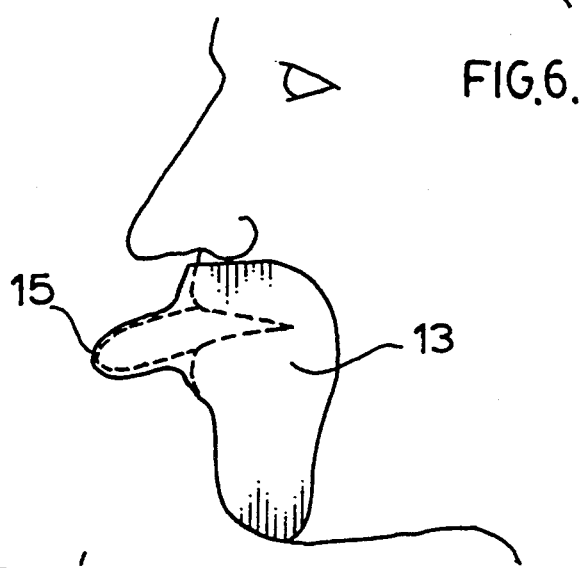

FIG. 1 shows a facial prophylactic generally indicated at 1. This facial prophylactic comprises a main body portion 3 which provides a facial cover as shown in FIGS. 2 and 3 of the drawings. This face cover as well as the remainder o the prophylactic is made from a stretchable material such as for example LATEX TM or SILICONE TM used for other types of prophylactics or condoms already available in the marketplace.

Provided generally centrally of the face cover is a region 5 integral with the face cover but made e.g. by thinning of the material to be more stretchable than the remainder of the face cover. This stretchable portion is bordered by a reinforced region 7 as shown in FIG. 1.

Also provided on the facial prophylactic are means for holding it tightly against a users face with these means being in the form of ear fitting openings 9. The entire facial prophylactic is shaped and sized such that with the ear fittings 9 in place, the facial prophylactic is pulled tightly up against ones face with the stretchable region 5 fitted directly over the mouth and allowing ones tongue to push outwardly of the main body portion of the face cover while still being covered by the stretchable portion. This is best seen in FIG. 3 of the drawings. Note that in the non-use position the stretchable region 5 lies in the same plane as the remainder of the facial prophylactic and the amount that it stretches is determined by and therefore suited for the particular individual using the prophylactic.

Figure 7:
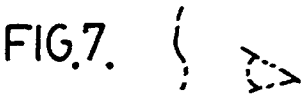
FIGS. 7 and 8 are sectional views through the facial prophylactic of FIGS. 5 and 6.

FIGS. 4 through 8 of the drawings show a modified version of the facial prophylactic generally indicated at 11. This particular prophylactic comprises a face cover portion 13 having a more stretchable portion or region 15. Note as seen in FIG. 7 of the drawings, the lower edge of the face cover extends down to a chin covering position and upwardly to a position just below the nose of the user.

Figure 8:
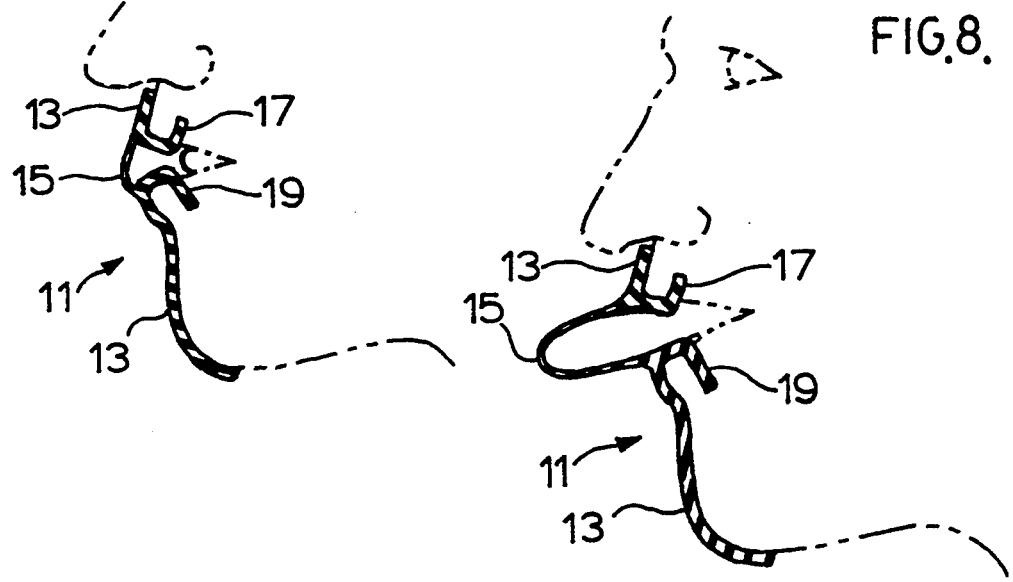

In this particular arrangement, the means for holding the facial prophylactic in position comprises upper and lower gum and lip fitting portions 17 and 19 respectively. There is an opening provided between portions 17 and 19 leaving the more stretchable region 15 exposed for tongue penetration through the face cover 15 while being covered by portion 15 as best seen in FIG. 8 of the drawings. Portions 17 and 19 are trapped between the gums and the lips as shown to hold the face cover in position. Different features may further be added to the facial prophylactic. For instance, the material used to make the prophylactic, i.e. material such as LATEX TM noted above can be flavored to avoid the otherwise undesirable taste of the LATEX TM . Furthermore, specific skin lubricants can be applied to the inside of the face cover to avoid chafing against the skin of the person wearing the face cover. The exterior surface of the face cover and in particular the more stretchable region can additionally be lubricated with lubricating materials similar to those found on a standard condom. In addition, the exterior surface of the more stretchable tongue receiving region on the facial prophylactic can be provided with ribbing or the like, again consistent with different condom designs.

FIG. 9 of the drawings is a sectional view through the mask of FIG. 1 and FIG. 10 is a sectional view through a mold during the manufacture of the mask shown in FIG. 1. According to this method of manufacture, a source 21 of liquid material M such as the LATEX TM or SILICONE TM earlier described, is poured or otherwise introduced to a mold 23 which defines the overall shape of the mask. While the material is still in the liquid state, i.e. before it is completely hardened, a nozzle 25 directs a controlled stream of air, as shown, downwardly onto the material in the mold and blows some of that material away from the area to which the stream of air is directed. This then produces a thinning of the material in this area resulting in the more stretchable tongue receiving area of the mask. The material which is blown away from the tongue receiving area forms the reinforced border 7 which is located at the outer surface of the mask while the remainder of the mask, i.e. the main mask portion peripherally of the tongue portion is unaffected and therefore remains thickened relative to the now thinned tongue receiving area.

According to the method shown in FIGS. 11 and 12, a material containing source 21 once again introduces a source of material M while in the liquid state to the mask shaping mold 23. The material is introduced in a manner so as to produce at least one initial layer of material L1 which completely covers the exposed face of the mold. From here in accordance with the next manufacturing step, a mechanical block 27 is placed atop the initial layer L1 before it is hardened and more material in the liquid state is introduced to the mold. This additional material forms at least one subsequent layer L2 which flows onto and bonds with layer L1 except in the area where layer L1 is covered by the mechanical block 27. The resultant mask 1a, as shown in FIG. 13 comprises a thinner tongue receiving portion 5a in the area covered by block 27 and a thicker main mask portion 3a peripherally of the tongue receiving portion.

It is to be appreciated that although the term layer is used to describe the construction of mask 1a, these layers are in both mechanically chemically bonded and therefore homogeneous with one another. Furthermore, there are no seams penetrating through the mask at the interface between the main mask portion and the tongue receiving portion. Accordingly, there is no opportunity for disease carrying liquids to pass through the mask.

Regardless of how the mask is manufactured, additional chemical processing may be carried out on the tongue receiving portion of the mask to further add to its elasticity relative to the main part of the mask.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A method of manufacturing a fluid impervious stretchable facial prophylactic mask having a main mask portion and a tongue receiving mask portion wherein the tongue receiving portion is thinner than co-planar with said main mask portion comprising providing a material in a liquid state, shaping said material to create a thinned area without penetrating said material and then hardening said material so that said thinned area forms said tongue receiving mask portion in a co-planar relationship to said main mask portion and so that said mask is free of any seams through said mask between said tongue receiving mask portion and said main mask portion.

2. A method as claimed in claim 1, including directing a controlled amount of pressure onto said material in a liquid state and moving a preset amount of said material through said pressure to create said thinned area which forms said tongue receiving portion upon hardening.

3. A method as claimed in claim 2, wherein said pressure is produced by a gas stream.

4. A method as claimed in claim 3, wherein the preset amount of material is blown away from said thinned area by the gas stream and, after hardening, the preset amount of material forms a reinforced region immediately around and defining said tongue receiving portion exteriorly of said mask.

5. A method as claimed in claim 1 wherein said material is introduced in the liquid state into a mask forming mold in stages, including at least one initial stage where the material covers all of said mask forming mold and forms an initial layer, and at least one subsequent stage in which a portion of the initial layer is blocked off during addition of the material in said at least one subsequent stage to create the thinned area at the blocked off portion.

6. A method as claimed in claim 1, including forming said mask from layers of said material comprising at least one initial layer including both said tongue receiving mask portion and said main mask portion and at least one subsequent layer including only said main mask portion and excluding said tongue receiving portion.

7. A method as claimed in claim 6, including excluding said tongue receiving portion from the at least one subsequent layer by blocking the formation of said at least one subsequent layer at the location where the tongue receiving portion is to be formed.

8. A method as claimed in claim 7, wherein blocking includes fitting a mechanical block over a portion of said at least one initial layer in which the thinned area is to be formed prior to introducing said at least one subsequent layer.

9. A method as claimed in claim 1, including forming a third mask portion thicker than and between said main mask portion and said tongue receiving mask portion.

10. A method as claimed in claim 1, further comprising treating said material with a flavoring agent.

11. A method as claimed in claim 1, including applying a skin lubricant to said material.

* * * * *